US012098164B2

(12) United States Patent
Lee et al.

(10) Patent No.: US 12,098,164 B2
(45) Date of Patent: Sep. 24, 2024

(54) NON-IMMUNOGENIC PROTEIN NANOPARTICLES WITH CANCER TARGETING ACTIVITY USING ALBUMIN-BINDING PEPTIDE

(71) Applicant: CELLEMEDY CO., LTD, Incheon (KR)

(72) Inventors: Jeewon Lee, Seoul (KR); Bo Ram Lee, Seoul (KR)

(73) Assignee: CELLEMEDY CO., LTD, Incheon (KR)

( * ) Notice: Subject to any disclaimer, the term of this patent is extended or adjusted under 35 U.S.C. 154(b) by 597 days.

(21) Appl. No.: 16/663,651

(22) Filed: Oct. 25, 2019

(65) Prior Publication Data
US 2020/0181204 A1    Jun. 11, 2020

(30) Foreign Application Priority Data
Oct. 26, 2018    (KR) ........................ 10-2018-0128849

(51) Int. Cl.
| | | |
|---|---|---|
| *C07K 14/005* | (2006.01) | |
| *A61K 9/51* | (2006.01) | |
| *A61K 33/242* | (2019.01) | |
| *A61K 38/00* | (2006.01) | |
| *A61K 38/38* | (2006.01) | |
| *A61K 49/00* | (2006.01) | |
| *C07K 16/18* | (2006.01) | |
| *C12N 7/00* | (2006.01) | |

(52) U.S. Cl.
CPC .......... *C07K 14/005* (2013.01); *A61K 9/5169* (2013.01); *A61K 9/5184* (2013.01); *A61K 33/242* (2019.01); *A61K 38/38* (2013.01); *A61K 49/0056* (2013.01); *A61K 49/0093* (2013.01); *C07K 16/18* (2013.01); *C12N 7/00* (2013.01); *A61K 38/00* (2013.01); *C07K 2319/31* (2013.01); *C07K 2319/735* (2013.01); *C12N 2710/10032* (2013.01); *C12N 2730/10122* (2013.01); *C12N 2730/10123* (2013.01)

(58) Field of Classification Search
None
See application file for complete search history.

(56) References Cited

FOREIGN PATENT DOCUMENTS

| KR | 10-2014-0133478 A | 11/2014 |
|---|---|---|
| KR | 10-1947092 B1 | 2/2019 |

OTHER PUBLICATIONS

Wang, Jue et al., "Binding of Serum Albumin on Tumor Cells and Characterization of the Albumin Binding Protein", *The Journal of Biochemistry*, vol. 115, Issue 5, May 1994, (pp. 898-903).
Dennis, Mark S. et al., "Albumin Binding as a General Strategy for Improving the Pharmacokinetics of Proteins", The Journal of Biological Chemistry, vol. 277, Issue 38, Sep. 20, 2002 (pp. 35035-35043).
Sato, Aaron K. et al., "Development of Mammalian Serum Albumin Affinity Purification Media by Peptide Phage Display", Biotechnology Progress, vol. 18, Issue 2, 2002 (pp. 182-192).
Office action issued on Mar. 8, 2021 from Korean Patent Office in a counterpart Korean Patent Application No. 10-2018-0128849 (all the cited references are listed in this IDS.) (English translation is also submitted herewith.).

*Primary Examiner* — Nicole Kinsey White
(74) *Attorney, Agent, or Firm* — The PL Law Group, PLLC

(57) ABSTRACT

The present invention relates to recombinant self-assembling protein nanoparticles presenting an albumin-binding peptide at the surface. For the recombinant self-assembling protein nanoparticles according to the present invention, an albumin-binding peptide can reduce the immunogenicity of the recombinant self-assembling protein nanoparticles because the albumin-binding peptide is presented at the surface, and thus binds to an albumin protein present in vivo, and the albumin-binding peptide can also provide the cancer delivery function of the recombinant self-assembling protein nanoparticles because the albumin-binding peptide binds to albumin around cancer. Simultaneously, the binding of the albumin-binding peptide to albumin can significantly increase the in vivo residence time of the recombinant self-assembling protein nanoparticles, thus increasing the potential for use in various medical applications.

12 Claims, 8 Drawing Sheets

Specification includes a Sequence Listing.

```
                        SEQUENCE LISTING

<160> NUMBER OF SEQ ID NOS: 9

<210> SEQ ID NO 1
    <211> LENGTH: 8
    <212> TYPE: PRT
    <213> ORGANISM: Artificial Sequence
    <220> FEATURE:
    <223> OTHER INFORMATION: FLAG tag

<400> SEQUENCE: 1

Asp Tyr Lys Asp Asp Asp Asp Lys
    1               5

<210> SEQ ID NO 2
    <211> LENGTH: 18
    <212> TYPE: PRT
    <213> ORGANISM: Artificial Sequence
    <220> FEATURE:
    <223> OTHER INFORMATION: Albumin binding peptide

<400> SEQUENCE: 2

Asp Asp Glu Trp Leu Cys Gly Trp Arg Pro Leu Cys Ile Asp Glu Ile
    1               5                   10                  15

Leu Arg

<210> SEQ ID NO 3
    <211> LENGTH: 6
    <212> TYPE: PRT
    <213> ORGANISM: Artificial Sequence
    <220> FEATURE:
    <223> OTHER INFORMATION: Histidine tag

<400> SEQUENCE: 3

His His His His His His
    1               5

<210> SEQ ID NO 4
    <211> LENGTH: 10
    <212> TYPE: PRT
```

```
<213> ORGANISM: Artificial Sequence
<220> FEATURE:
<223> OTHER INFORMATION: Linker

<400> SEQUENCE: 4

Gly Gly Gly Gly Ser Gly Thr Thr Thr Thr
1               5                   10

<210> SEQ ID NO 5
<211> LENGTH: 22
<212> TYPE: PRT
<213> ORGANISM: Artificial Sequence
<220> FEATURE:
<223> OTHER INFORMATION: Linker

<400> SEQUENCE: 5

Ala Ser Ser Leu Arg Gln Ile Leu Asp Ser Gln Lys Met Glu Trp Arg
1               5                   10                  15

Ser Asn Ala Gly Gly Ser
            20

<210> SEQ ID NO 6
<211> LENGTH: 15
<212> TYPE: PRT
<213> ORGANISM: Artificial Sequence
<220> FEATURE:
<223> OTHER INFORMATION: Linker

<400> SEQUENCE: 6

Gly Gly Gly Ser Gly Gly Thr Gly Gly Ser Gly Gly Gly
1               5                   10              15

<210> SEQ ID NO 7
<211> LENGTH: 6
<212> TYPE: PRT
<213> ORGANISM: Artificial Sequence
<220> FEATURE:
<223> OTHER INFORMATION: Linker

<400> SEQUENCE: 7

Tyr Tyr Tyr Tyr Tyr Tyr
1               5

<210> SEQ ID NO 8
<211> LENGTH: 57
<212> TYPE: PRT
<213> ORGANISM: Artificial Sequence
<220> FEATURE:
<223> OTHER INFORMATION: affibody peptide

<400> SEQUENCE: 8

Val Asp Asn Lys Phe Asn Lys Glu Met Trp Ala Ala Trp Glu Ile
1               5                   10                  15

Arg Asn Leu Pro Asn Leu Asn Gly Trp Gln Met Thr Ala Phe Ile Ala
                20                  25                  30

Ser Leu Val Asp Asp Pro Ser Gln Ser Ala Asn Leu Ala Glu Ala Lys
            35                  40                  45

Lys Leu Asn Asp Ala Gln Ala Pro Lys
        50                  55

<210> SEQ ID NO 9
<211> LENGTH: 148
<212> TYPE: PRT
<213> ORGANISM: Hepatitis B virus
```

```
<400> SEQUENCE: 9

Asp Ile Asp Pro Tyr Lys Glu Phe Gly Ala Ser Val Glu Leu Leu Ser
1               5                   10                  15

Phe Leu Pro Ser Asp Phe Phe Pro Ser Ile Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Asn Leu Ala Thr Trp Val Gly Ser Asn Leu Glu Asp Pro Ala Ser
65                  70                  75                  80

Arg Glu Leu Val Val Ser Tyr Val Asn Val Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
            115                 120                 125

Pro Ala Tyr Arg Pro Pro Asn Ala Pro Ile Leu Ser Thr Leu Pro Glu
        130                 135                 140

Thr Thr Val Val
145
```

NON-IMMUNOGENIC PROTEIN NANOPARTICLES WITH CANCER TARGETING ACTIVITY USING ALBUMIN-BINDING PEPTIDE

CROSS-REFERENCE TO RELATED APPLICATION

This application claims priority to and the benefit of Korean Patent Application No. 10-2018-0128849, filed on Oct. 26, 2018, the disclosure of which is incorporated herein by reference in its entirety.

BACKGROUND

1. Field of the Invention

The present invention relates to non-immunogenic protein nanoparticles with cancer targeting activity using an albumin-binding peptide, and a use thereof.

2. Discussion of Related Art

Although protein nanoparticles (PNPs) (for example: viral capsid protein nanoparticles) capable of delivering a broad range of drugs have shown distinct advantages such as high biodegradability and remarkably low nanotoxicity when injected in vivo over synthetic nanoparticles, PNPs have an intrinsic drawback that hampers their clinical application, that is, potential immunogenicity. Protein nanoparticles developed for medical field applications have an immunogenic site that is recognized as an external substance by various immune cells when the protein nanoparticles are applied in vivo, and are absorbed and decomposed by macrophages and the like due to the site, and thus lose their functions and are released ex vivo and modified in vivo in some cases. In particular, heterologous protein nanoparticles carrying a large amount of immunogenic sites are highly likely to show immunotoxicity caused by an immune response. Accordingly, when the immunogenicity of protein nanoparticles is removed, the protein nanoparticles may be used as an effective drug carrier and bioimaging material.

Albumin is a protein in the body, which accounts for about 50% of serum, and does not induce an immune response by immune cells. Therefore, when the immunogenic site of protein nanoparticles injected with serum albumin present in the body is shielded, the immune response that may be induced in the body can be dramatically reduced/eliminated. Further, the in vivo residence time of protein nanoparticles may be dramatically increased by suppressing the immune response, and through this, protein nanoparticles may be more effectively used as therapeutic nanomaterials. In addition, in vivo albumin is known as a protein essential for the growth of not only normal cells, but also cancer cells. Accordingly, it has been reported that when primary cancer is formed in the body, the primary cancer absorbs in vivo serum albumin in large amounts during growth and future metastasis. As a part of these studies, there is a report of selecting an optimal serum albumin binding-inducing peptide having high binding efficiency with albumin (*Biotechnol. Prog.* 18, 182, 2002; Non-Patent Document 1), but the report has a limitation in that the selected peptide is merely artificially combined with an existing antibody and used for cancer diagnosis.

SUMMARY OF THE INVENTION

The present invention has been made in an effort to provide recombinant self-assembling nanoparticles presenting an albumin-binding peptide at the surface, so as to overcome the limitation of protein nanoparticles having potential immunogenicity.

The present invention has also been made in an effort to provide various medical uses of recombinant self-assembling protein nanoparticles presenting an albumin-binding peptide at the surface.

The present invention provides recombinant self-assembling protein nanoparticles presenting an albumin-binding peptide at the surface.

As a result of incessant studies to clinically apply protein nanoparticles having distinct advantages such as high biodegradability and remarkably low nanotoxicity when injected in vivo over synthetic nanoparticles, the present inventors expected that an albumin-binding peptide could reduce the immunogenicity of protein nanoparticles if the immunogenic site of protein nanoparticles could be shielded by albumin present in vivo. Further, since the albumin-binding peptide may bind to albumin present in a large amount at a cancer site, it was expected that protein nanoparticles could be targeted to cancer.

Based on this hypothesis, the present inventors induced binding with the albumin protein in vivo as an example of protein nanoparticles by presenting an albumin-inducing peptide at an immunogenic site of heterologous protein hepatitis B virus capsid nanoparticles which have an excellent advantage as a material for drug delivery and in vivo imaging diagnosis, but are difficult to use as therapeutic nanomaterials because an immune response is present when the protein nanoparticles are injected in vivo, and as a result, the present inventors proved an effect of reducing in vivo immunogenicity of virus capsid protein nanoparticles. Further, the present inventors also proved the cancer delivery function of protein nanoparticles by inducing an albumin binding-inducing peptide to bind to albumin around cancer with protein nanoparticles injected in vivo.

Thus, the present invention provides recombinant self-assembling protein nanoparticles presenting an albumin-binding peptide at the surface.

As used herein, the term "self-assembling protein" refers to a protein and a subunit or peptide of the protein, in which when a number of proteins and subunits or peptides of the proteins are gathered, they form an aggregate by forming an organized structure or pattern by themselves. These self-assembling proteins enable nanoparticles of a protein to be formed, and thus may be advantageously used in the preparation of the protein nanoparticles according to the present invention.

The self-assembling protein may be fused with a heterologous peptide or heterologous protein, and the heterologous peptide or heterologous protein may be located inside or outside during self-assembly according to purpose.

Since the albumin-binding peptide in the present invention serves to provide a region capable of binding to albumin in vivo in order to shield an immunogenic site of self-assembling protein nanoparticles, the albumin-binding peptide is regulated so as to be located outside during the self-assembly of the self-assembling protein nanoparticles. The site where the albumin-binding peptide is fused such that the albumin-binding peptide may be located outside the fusion protein may vary depending on the type of self-assembling protein, and may be appropriately selected by a person skilled in the art.

Further, a linker or the like may be used if necessary to help allow the albumin-binding peptide to be presented at the surface of the self-assembling protein nanoparticles. Accordingly, an exemplary embodiment of the present invention provides recombinant self-assembling protein nanoparticles further including a linker peptide at the albumin-binding peptide. The linker peptide may have an appropriate length to aid in surface presentation of the albumin-binding peptide. For example, the linker peptide may be a peptide consisting of 5 to 20, for example, 5 to 15 amino acids, and one or more linker peptides may be used in one monomer of the recombinant self-assembling protein. The linker peptide may be a non-reactive peptide, and for example, a peptide including multiple glycines may be used as the linker peptide.

The present invention also provides recombinant self-assembling protein nanoparticles including a gold ion adsorbable peptide and a superparamagnetism-inducing peptide. According to the content disclosed in Korean Patent Application No. 10-2017-0084793 by the present inventors, recombinant self-assembling protein nanoparticles including a gold ion adsorbable peptide and a superparamagnetism-inducing peptide enable a superparamagnetic gold nanoparticle cluster-protein nanoparticle fusion body to be prepared by forming superparamagnetic ultramicro gold particles on protein nanoparticles. Since the superparamagnetic gold nanoparticle cluster-protein nanoparticle fusion body has a targeted directional magnetic thermotherapy effect and a contrast effect for magnetic resonance imaging, medical utilization is high.

The gold ion adsorbable peptide has characteristics of adsorbing a gold ion provided in the form of a gold precursor. The gold ion adsorbable peptide may be used regardless of any sequence as long as the gold ion adsorbable peptide has gold ion adsorption characteristics. In an embodiment, the gold ion adsorbable peptide may consist of an amino acid sequence including a plurality of histidines (Hn, n≥2), but is not limited thereto. In an embodiment, the gold ion adsorbable peptide may be introduced at the N-terminus, spike site, or C-terminus of a recombinant HBV core protein, but is not limited thereto. If the albumin-binding peptide is introduced at the spike site of the recombinant HBV core protein, it is possible to simultaneously fuse a gold ion adsorbable peptide and the albumin-binding peptide onto one monomer of the HBV core protein by introducing the gold ion adsorbable peptide at the C-terminus of the recombinant HBV core protein. In contrast, a fusion protein may also be expressed such that the albumin-binding peptide and the gold ion adsorbable peptide are fused to monomers of respectively different HBV core proteins.

Meanwhile, the recombinant self-assembling protein nanoparticles may further include a superparamagnetism-inducing peptide. The superparamagnetism-inducing peptide may be used regardless of any sequence as long as the peptide is capable of charge transfer, such that the superparamagnetism may be induced in gold nanoparticles. In an embodiment, the superparamagnetism-inducing peptide may consist of an amino acid sequence including a plurality of tyrosines (Yn, n≥2) or cysteines (Cn, n≥2).

Korean Patent Application No. 10-2017-0084793 may be referenced for other specific details such as a method for forming superparamagnetic gold nanoparticles.

The recombinant self-assembling protein nanoparticles of the present invention may further include a target-oriented peptide. The target-oriented peptide refers to a peptide capable of binding to the surface of cells such as cancer cells or inflammatory cells, such that the recombinant self-assembling protein nanoparticles according to the present invention can move to a target site in vivo, which requires treatment or diagnosis, such as cancer cells or inflammatory cells. The recombinant self-assembling protein nanoparticles according to the present invention includes an albumin-binding peptide, and thus have the target directivity for all cancer cells without using a target-oriented peptide. However, when the recombinant self-assembling protein nanoparticles according to the present invention are targeted to a site other than cancer, such as inflammation, a target-oriented peptide may be utilized. In this case, the target-oriented peptide may be introduced so as to be presented at the surface of recombinant self-assembling protein nanoparticles. In an embodiment of the present invention, the target-oriented peptide may be introduced at the N-terminus, spike site, or C-terminus of a recombinant HBV core protein. More specifically, the target-oriented peptide may be introduced at a spike site of a recombinant HBV core protein, for example, between the 1-77th amino acid sequence part and the 81-148th amino acid sequence part.

In an embodiment, to facilitate isolation and purification, the recombinant self-assembling protein nanoparticles may further include a peptide for isolation and purification, such as a histidine tag, a DYKDDDDK(FLAG) tag(SEQ ID NO: 1), and a GST tag. The peptides for isolation and purification are fused at appropriate sites so as to be located outside the self-assembling protein nanoparticles.

As the self-assembling protein previously described, but it is possible to use a hepatitis B virus core protein, a tobacco mosaic virus protein, a *Thermoplasma acidophilum*-derived proteasome (tPTS), or an *Escherichia coli*-derived DNA binding protein (eDPS), and the like, but the present invention is not limited thereto.

In an embodiment of the present invention, a hepatitis B virus core protein (hereinafter, referred to as 'HBVC') may be used as self-assembling protein nanoparticles. The hepatitis B virus core protein is also referred to as a hepatitis B virus capsid protein, and is a spherical protein nanoparticle formed by self-assembly of 180 or 240 capsid monomers. In the present invention, the hepatitis B virus core protein may refer to a spherical protein nanoparticle formed by self-assembly of capsid monomers, or respective capsid monomers forming the protein nanoparticles. When 240-16 kDa capsid protein monomers are self-assembled in cells, spherical nanoparticles with a diameter of about 36 nm are formed. Each capsid monomer is expressed in the form of a fusion protein including an albumin-binding inducing peptide, and then self-assembled to form protein nanoparticles.

For example, the HBVC protein nanoparticles (HBVC-ABP) including the albumin-binding peptide (ABP) may be prepared by a preparation method including: a) obtaining HBVC protein gene-derived genetic clone, b) preparing a clone including an albumin-binding inducing peptide to be presented at the surface of the HBVC protein, c) preparing an expression vector through ligation of the prepared gene clone, and d) expressing a recombinant HBVC-ABP protein by transforming a host with the expression vector.

According to the present invention, it is possible to reproducibly mass-produce recombinant protein nanoparticles showing a very uniform particle size distribution. In addition, since these recombinant protein nanoparticles are a biocompatible material that may be decomposed after being used in vivo, there is no toxicity problem due to remaining nanoparticles.

When the HBV core protein is fused to a heterologous protein at the spike site, N-terminus, or C-terminus to express a fusion protein, the expressed heterologous protein may be presented at the outer surface of protein nanoparticles. Since the recombinant hepatitis B virus capsid protein of the present invention imparts an albumin-binding peptide, and the like to protein nanoparticles by a genetic engineering method instead of a chemical method, there are advantages in that the surface presentation frequency and position thereof may be controlled as desired and the modification of biological activity may be minimized.

Accordingly, an embodiment of the present invention provides recombinant self-assembling protein nanoparticles in which a recombinant self-assembling protein is a hepatitis B virus core protein, and an albumin-binding peptide is located at a spike site of the hepatitis B virus core protein.

In the present invention, the albumin-binding peptide refers to a peptide capable of binding to an albumin present in vivo, and it is possible to use a publicly known albumin-binding peptide known to have binding capability with albumin. In an embodiment of the present invention, one (DDEWLCGWRPLCIDEILR) (SEQ ID NO: 2) (J. Biol. Chem. 2002, 277, 35035.) of the publicly known albumin-binding peptides was used, but is not limited thereto.

For the purpose of the present invention, the albumin-binding peptide may be introduced so as to be presented at the surface of the recombinant hepatitis B virus (HBV) capsid protein nanoparticles. In an embodiment of the present invention, the albumin-binding peptide may be introduced at the spike site of recombinant HBV capsid nanoparticles. More specifically, the albumin-binding peptide may be introduced between the 1-77th amino acid sequence part and the 81-148th amino acid sequence part, of the recombinant HBV capsid monomer. An example of the present invention shows that the immunogenicity can be suppressed through binding with albumin in vivo by introducing the albumin-binding peptide at the spike site of the recombinant HBV capsid protein.

In the following Examples, to reduce the immunogenicity of protein nanoparticles, the corresponding protein nanoparticles were prepared by presenting an albumin-binding inducing peptide DDEWLCGWRPLCIDEILR (SEQ ID NO: 2) (hereinafter, referred to as ABP) at the surface of a surface spike part (HBVC Asp77-Arg81) of a heterologous protein *E. coli* Hepatitis B virus core antigen (hereinafter, referred to as HBVC) which has an excellent advantage as a material for drug delivery and in vivo imaging diagnosis, but is difficult to use as a therapeutic nanomaterial because an immune response is present when the heterologous protein is injected in vivo. During the preparation of the protein nanoparticles, a glycine linker was added to the Asp77-Arg81 part of the HBVC to effectively present the ABP at the surface, and induced so as to bind to serum albumin in vivo during the self-assembly of the protein, thereby leading to fusion and expression.

When the HBVC-ABP fusion protein nanoparticles developed by the present invention induce in vivo serum albumin to bind onto the surface of the nanoparticles, the immunogenic site of the HBVC surface is shielded by the serum albumin, and thus an effect of reducing an immune response may be expected.

In an embodiment of the present invention, it is shown that when HBVC particles in which a serum albumin-binding inducing peptide is presented at the surface are actually injected in vivo, immunogenicity is remarkably reduced as compared to the protein nanoparticles of HBVC itself.

Further, the HBVC-ABP protein nanoparticles according to the present invention, through injection of particles in vivo, are actually more effective in the U87MG glioma cancer targeting than the HBVC, and when particles are injected in vivo, the ABP on the surface of the HBVC binds to the serum albumin in vivo to show an effect of reducing the immunogenicity of protein nanoparticles themselves.

In addition, since albumin is a protein essential for the growth of not only normal cells, but also cancer cells, it has been reported that when primary cancer is formed in vivo, the primary cancer absorbs in vivo serum albumin in large amounts during growth and future metastasis (*J. Biochem.* 1994, 115, 898; *Antic ancer Res.* 1990, 10, 343). Accordingly, when HBVC-ABP particles are labeled with a labeling material for imaging and introduced in vivo, the HBVC-ABP particles can be used as a material for imaging cancer in vivo. When only the ABP itself is injected in vivo, only the peptide itself is injected in vivo, and thus is rapidly decomposed in vivo, so that the imaging effect cannot be obtained.

According to an embodiment of the present invention, it is possible to prepare a monomer of a HBV core protein in which an albumin-binding peptide is located at a spike site of a HBV core protein, that is, between the 1-77th amino acid sequence part and the 81-148th amino acid sequence part of the core protein, and a histidine tag binds to the N-terminal part of the HBV core protein. When 180-240 of these monomers are self-assembled, it is possible to form recombinant self-assembling protein nanoparticles presenting an albumin-binding protein and a histidine tag at the surface.

Furthermore, recombinant self-assembling protein nanoparticles may also be prepared using characteristics in which the amino terminus and carboxyl terminus of the self-assembling protein are presented at the surface. For example, it is also possible to fuse a peptide such as an albumin-binding peptide or a protein to the N-terminus or C-terminus of the HBV core protein.

Further, it is also possible to bind various compounds according to purpose, such as a fluorescent material and various drugs for diagnosis or treatment to the surfaces of the recombinant self-assembling protein nanoparticles through a chemical process.

Meanwhile, the recombinant self-assembling protein nanoparticles may be in a form in which two or more different monomers are self-assembled. When the recombinant self-assembling protein nanoparticles consist of different monomers, the surface of the recombinant self-assembling protein nanoparticles may be prepared in a more diverse way.

For example, provided are recombinant self-assembling nanoparticles in which the recombinant self-assembling protein is a hepatitis B virus core protein, and the albumin-binding peptide is fused to some monomers of the hepatitis B virus core protein. A monomer of the recombinant self-assembling protein including the albumin-binding peptide may be included in order to reduce immunogenicity and/or impart cancer cell-targeting. By including a separate target-oriented peptide in other monomers or including a gold ion adsorbable peptide and a superparamagnetism-inducing peptide, it is possible to deliver a drug to a specific target or utilize the drug for magnetic thermotherapy or magnetic resonance imaging, and the like.

In an embodiment, a virus-derived protein may be used as the self-assembling protein. The virus-derived self-assembling protein or protein nanoparticles including the same may attain self-assembly in various shapes (disk or rod shape) and various sizes. The virus-derived protein may be a tobacco mosaic virus (hereinafter, also referred to as 'TMV').

According to an embodiment of the present invention, the TMV may bind the albumin-binding peptide, and the like to both termini thereof. For example, the albumin-binding peptide may be fused to the TMV N-terminus and C-terminus. The albumin-binding peptide fused to the TMV may be presented at the surface of the protein nanoparticles to reduce immunogenicity and to impart target directivity to cancer cells.

As another example, a *Thermoplasma acidophilum*-derived proteasome (hereinafter, referred to as 'tPTS') may be used as the self-assembling protein. The tPTS can be expressed in *Escherichia coli* using genetic recombination technology, while 14 alpha proteins and 14 beta proteins having different sequences form protein nanoparticles in an approximately cylindrical form by self-assembly. The protein nanoparticles show very high thermal stability, and the amino terminus and carboxyl terminus of the alpha protein and the carboxyl terminus of the beta protein are presented at the outside, and thus, when a heterologous protein is fused and expressed at each part, the heterologous protein is characterized as being presented at the surface of the protein nanoparticles. Although the present invention is not limited thereto, an albumin-binding peptide may bind to the N-terminus or C-terminus of the tPTS.

As another example, an *Escherichia coli*-derived DNA binding protein (hereinafter, referred to as 'eDPS') may be used as the self-assembling protein. The eDPS forms spherical protein nanoparticles with a size of 8 to 10 nm by self-assembly of 12 identical monomers. The spherical protein nanoparticles can be mass-expressed in *Escherichia coli* using genetic recombination technology, and the amino terminus and carboxyl terminus thereof are presented at the surface, and thus can be fused and expressed for the presentation of a heterologous protein. Although the present is not limited thereto, an albumin-binding peptide may bind to the N-terminus or C-terminus of the eDPS.

Since the recombinant self-assembling protein nanoparticles are spherical protein particles having a nanometer-sized diameter, and form particles by the self-assembly of the self-assembling protein, particles showing a very uniform particle size distribution may be reproducibly prepared, and the recombinant self-assembling protein nanoparticles are a biocompatible material which may be decomposed after being used in vivo, so that there is no toxicity problem due to remaining nanoparticles after the recombinant self-assembling protein nanoparticles are used for medical use.

In particular, since the recombinant self-assembling protein nanoparticles of the present invention may bind to albumin present in vivo, and thus may reduce immunogenicity, the recombinant self-assembling protein nanoparticles can be applied in vivo more safely, and are particularly excellent in an effect of targeting cancer sites where albumin is distributed in large amounts.

Accordingly, the present invention also provides a non-immunogenic medical composition including: the recombinant self-assembling protein nanoparticles according to the present invention; and a pharmaceutically acceptable carrier.

The medical composition may further include an active ingredient suitable for the purpose of treatment, prevention, or diagnosis. For example, it is possible to bind an active ingredient suitable for the purpose of treatment to the N-terminus or C-terminus of the recombinant self-assembling protein nanoparticles, or to encapsulate or bind an active ingredient inside or to the inner side of the recombinant self-assembling protein. Although a disease related to the treatment, prevention, or diagnosis is not particularly limited, in an embodiment, the active ingredient may be an active ingredient for the purpose of diagnosis, prevention, or treatment of cancer due to the target directivity of the albumin-binding peptide to cancer.

The pharmaceutically acceptable carrier includes a carrier and a vehicle typically used in the medical field, and specific examples thereof include an ion exchange resin, alumina, aluminum stearate, lecithin, a serum protein (for example, human serum albumin), a buffer substance (for example, various phosphates, glycine, sorbic acid, potassium sorbate, partial glyceride mixture of saturated vegetable fatty acid), water, a salt or electrolyte (for example, protamine sulfate, disodium hydrogen phosphate, potassium hydrogen phosphate, sodium chloride, and zinc salts), colloidal silica, magnesium trisilicate, polyvinylpyrrolidone, cellulose-based substrate, polyethylene glycol, sodium carboxymethylcellulose, polyarylate, wax, polyethylene glycol, wool, or the like, but are not limited thereto. In addition, a contrast agent composition of the present invention may further include a lubricant, a wetting agent, an emulsifier, a suspending agent, a preservative, or the like, in addition to the aforementioned ingredients.

Furthermore, the recombinant self-assembling nanoparticles of the present invention enables target directivity to cancer cells or tissues carrying albumin in large amounts due to the albumin-binding peptide, and thus may be used as a contrast agent capable of imaging a target site through magnetic resonance and an optical imaging device.

Accordingly, the present invention provides a contrast agent composition including: recombinant self-assembling protein nanoparticles; a labeling material for imaging; and a pharmaceutically acceptable carrier.

As the labeling material for imaging, a T1/T2 magnetic resonance imaging diagnostic probe, an optical diagnostic probe, a CT diagnostic probe, a radioactive isotope, or the like may be used.

As an aspect, the medical composition or contrast agent composition according to the present invention may be prepared using an aqueous solution for parenteral administration, and preferably, a buffer solution such as Hank's solution, Ringer's solution or a physically buffered saline solution may be used. In an aqueous injection suspension, a substrate capable of increasing the viscosity of the suspension, such as sodium carboxymethyl cellulose, sorbitol or dextran may be added.

In another preferred aspect, the medical composition or contrast agent composition of the present invention may be in the form of a sterile injectable preparation of a sterile injectable aqueous or oily suspension. The suspension may be formulated according to publicly known technology using a suitable dispersant or wetting agent (for example, Tween 80) and a suspending agent.

Further, the sterile injectable preparation may be a sterile injectable solution or suspension in a non-toxic parenterally-acceptable diluent or solvent (for example, a solution in 1,3-butanediol). Examples of a vehicle and a solvent that may be used include mannitol, water, Ringer's solution, and an isotonic sodium chloride solution. Furthermore, sterile, non-volatile oils are typically used as a solvent or suspending medium. Any mild non-volatile oil, including synthetic mono- or diglycerides, may be used for this purpose.

The benefits and features of the present invention, and the methods of achieving the benefits and features will become apparent with reference to exemplary embodiments to be described below in detail. However, the present invention is not limited to the exemplary embodiments to be disclosed below and may be implemented in various other forms, and the present exemplary embodiments are only provided for rendering the disclosure of the present invention complete and for fully conveying the scope of the invention to a person with ordinary skill in the technical field to which the

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
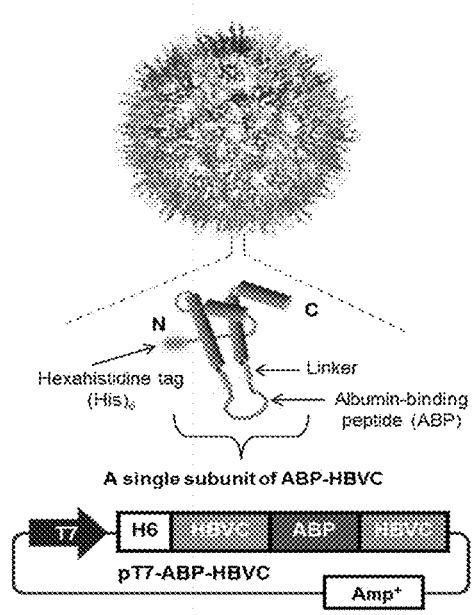
FIG. 1 is a schematic view illustrating the structure of a hepatitis B virus capsid protein nanoparticle including an albumin-binding peptide according to the present invention.

[Example 1] Construction of Expression Vector for Biosynthesis of HBV Capsid-Derived Nanoparticles FIG. 1 is a schematic view illustrating the structure of a hepatitis B virus capsid protein nanoparticle (HBVC-ABP) including an albumin-binding peptide according to the present invention.

According to the vector schematic view described in the following Table 1, hepatitis B virus capsid protein nanoparticles (HBVC) and hepatitis B virus capsid protein nanoparticles (HBVC-ABP) including the albumin-binding peptide according to the present invention were prepared through PCR. All prepared plasmid expression vectors were purified on an agarose gel, and then the sequence was confirmed through complete DNA sequencing.

An expression vector capable of expressing the respective protein nanoparticles was constructed by sequentially inserting the PCR products thus prepared into a pT7-7 expression vector.

The expression vectors of the respective protein nanoparticles proceeded as pT7-HBVC and pT7-HBVC-ABP.

A clone encoding the synthesis of N-NdeI-H6 (hexahistidine) (SEQ ID NO: 3)-HBVcAg(1-77)-linker(G4SG4T) (SEQ ID NO: 4)-ABP (DDEWLCGWRPLCIDEILR) (SEQ ID NO: 2)HBVcAg(81-148) linker (G4SG4T) (SEQ ID NO: 4)-ClaI-C was obtained by inserting an albumin-binding peptide (DDEWLCGWRPLCIDEILR) (SEQ ID NO: 2) instead of Asp77-Arg81 which is the loop 77-81$^{st}$ amino acid sequence between HBV core protein (HBVC) genes.

Further, in order to verify the actual cancer targeting capability of actual ABP, the present inventors used HBVC-affi+ particles that had already been verified for cancer targeting capability in the Examples. For the HBVC-affi+ particles configured by the present inventors in the past, a vector was constructed so as to facilitate surface presentation by tandem insertion of an affibody binding to an epidermal growth factor receptor (EGFR) known to be overexpressed in cancer into the loop 77-81$^{st}$ amino acid sequence between HBV core protein (HBVC) genes at a spike and inserting a linker at both ends of the affibody. The aforementioned vector is as follows. NH2-H6 (SEQ ID NO: 3)-linker 1 (ASSLRQILDSQKMEWRSNAGGS) (SEQ ID NO: 5)-linker 2 (G3S G3TG3SG3) (SEQ ID NO: 6)-Y6 (SEQ ID NO: 7)-HBVcAg (1-77)-linker 3 (G4SG4T) (SEQ ID NO: 4) (affibody peptide (VDNKFNKEMWAAWEEIRNLPNLNGWQMTAFIASLVDDPSQSAN LAEAKKLNDAQAPK)2(SEQ ID NO: 8)-linker 4-HBVcAg (81-148)-COOH

TABLE 1

Construct of expression vector for each nanoparticle

| Protein nanoparticle | Expression vector |
|---|---|
| HBVC | NH$_2$-NdeI-H6(SEQ ID NO: 3)-HBVC-ClaI-COOH |
| HBVC-ABP | , NH$_2$-NdeI-H6(hexahistidine)(SEQ ID NO: 3)-HBVcAg(1-77)-linker(G4SG4T)(SEQ ID NO: 4)-ABP(DDEWLCGWRPLCIDEILR)(SEQ ID NO: 2)-HBVcAg(81-148)-linker(G4SG4T)(SEQ ID NO: 4)-ClaI-COOH |
| HBVC-affi+ | NH2-H6(SEQ ID NO: 3)- linker 1 (ASSLRQILDSQKMEWRSNAGGS)(SEQ ID NO: 5)- linker 2 (G3S G3TG3SG3)(SEQ ID NO: 6)-Y6(SEQ ID NO: 7)-HBVcAg (1-77)- linker 3 (G4SG4T)(SEQ ID NO: 4)-(affibody peptide (VDNKFNKEMWAAWEEIRNLPNLNGWQMTAFIASLVDDPSQSANLAEAKKLNDAQAPK)2 (SEQ ID NO: 8)- linker 4-HBVcAg (81-148)-COOH |

[Example 2] Biosynthesis of Candidate Protein Nanoparticles

An *E. coli* strain BL21(DE3)[F-ompThsdSB(rB-mB-)] was each transformed with the prepared expression vector, and ampicillin-resistant transformants were selected. The transformed *E. coli* was cultured in flasks (250 mL Erlenmeyer flasks, 37° C., 150 rpm) containing 50 mL of a Luria-Bertani (LB) medium (containing 100 mgL-1 ampicillin). When medium turbidity (OD600) reached about 0.4 to 0.5, the expression of the recombinant gene was induced by adding isopropyl-β-D-thiogalactopyranosid (IPTG) (1.0 mM) and biotin (100 uM) for biotinylation at the N-terminus of the protein. After culturing at 20° C. for 16 to 18 hours, a bacterial cell precipitate was collected by centrifuging the cultured *E. coli* at 4,500 rpm for 10 minutes, and then suspended in 5 ml of a lysis solution (10 mM Tris-HCl buffer, pH 7.5, 10 mM EDTA) and disrupted using an ultrasonic cell disruptor (Branson Ultrasonics Corp., Danbury, CT, USA). After disruption, centrifugation was performed at 13,000 rpm for 10 minutes, and then the supernatant and the insoluble aggregate were separated. Purification was performed according to Example 3 using the separated supernatant.

[Example 3] Purification of Protein Nanoparticles and Attachment of Fluorescent Material The supernatant obtained in Example 2 was purified through a 3-step process. First, 1) Ni2+-NTA affinity chromatography using binding of histidine and nickel fused and expressed in the recombinant protein, and then 2) the recombinant protein was concentrated and a fluorescent material was attached through buffer exchange, and 3) finally, sucrose gradient ultracentrifugation was performed in order to separate only the self-assembled protein nanoparticles to which the fluorescent material was attached. Detailed description for each step is as follows.
1) Ni2+-NTA Affinity Chromatography
In order to purify the recombinant protein, the cell pellet was re-suspended in 5 mL of a lysis buffer (pH 8.0, 50 mM sodium phosphate, 300 mM NaCl, 20 mM imidazole) by collecting cultured *E. coli* by the same method described above, and cells were disrupted using an ultrasonic cell disruptor. After only the supernatant was separated by centrifuging the disrupted cell solution at 13,000 rpm for 10 minutes, each recombinant protein was separated using Ni2+-NTA columns (Qiagen, Hilden, Germany) (wash buffer: pH 8.0, 50 mM sodium phosphate, 300 mM NaCl, 80 mM imidazole/elution buffer: pH 8.0, 50 mM sodium phosphate, 300 mM NaCl, 200 mM imidazole).
2) Concentration and Buffer Exchange and Fluorescent Material Attachment Processes
3 ml of the recombinant protein eluted through Ni2+-NTA affinity chromatography was put into a ultracentrifugal filter (Amicon Ultra 100K, Millipore, Billerica, MA), and centrifuged at 5,000 g until 1 ml of the solution remained on the column at 5,000 g. Thereafter, in order to attach cy5.5 which is an NIR fluorescent material, the protein particles were subjected to buffer exchange with a sodium bicarbonate (0.1M, pH 8.5) buffer, and a fluorescent material was attached at room temperature for 12 hours.
3) Sucrose Gradient Ultra-High Speed Centrifugation
After a solution including 60%, 50%, 40%, 30%, and 20% sucrose was each prepared by adding sucrose at each concentration to a PBS (2.7 mM KCl, 137 mM NaCl, 2 mM KH2PO4, 10 mM Na2HPO4, pH7.4) buffer, 2 ml of the sucrose solution at each concentration (60 to 20%) was each put into tubes for ultra-high speed centrifugation (Ultra-Clear 13.2 ml tube, Beckman) starting from the solution at high concentration, and then after the tubes were filled with 1 ml of the recombinant protein solution present in the prepared buffer for self-assembly, ultra-speed centrifugation was performed at 4° C. and 35,000 rpm for 16 hours (Ultracentrifuge L-90k, Beckman). After centrifugation, a pipette was carefully used to replace the buffer of the recombinant in the upper layer (40 to 50% sucrose solution part) using an ultracentrifugal filter and a PBS buffer as specified in 2).

[Example 4] Analysis of Structure of Prepared Protein Nanoparticles

In order to analyze the structure of the recombinant protein nanoparticles purified after being subjected to the aforementioned process, the recombinant protein was photographed by a transmission electron microscope (TEM). First, a purified protein sample which had not been stained was placed on carbon-coated copper electron microscope grids, and then naturally dried. In order to obtain stained images of the protein nanoparticles, electron microscope grids including the naturally dried sample were incubated with a 2% (w/v) aqueous uranyl acetate solution at room temperature for 10 minutes, and washed three to four times with distilled water. Protein nanoparticle images were observed using Philips Technai 120 kV electron microscope. In addition, the sizes of the nanoparticles were measured through a dynamic light scattering (DLS) analysis.

Figure 2:
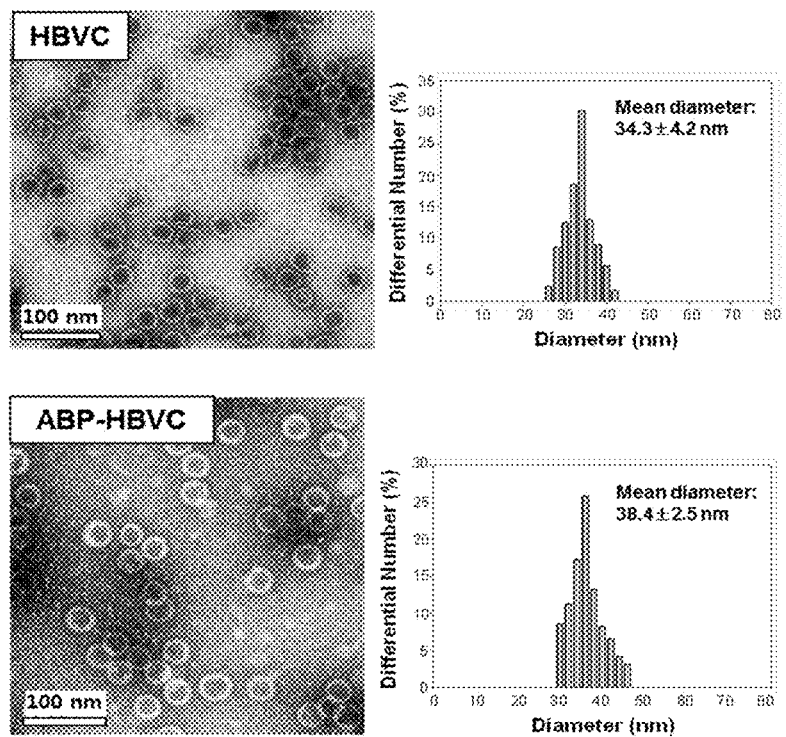
FIG. 2 is a set of transmission electron microscope (TEM) photographs of hepatitis B virus capsid protein nanoparticles (HBVC) and hepatitis B virus capsid protein nanoparticles (HBVC-ABP) including an albumin-binding peptide and a set of graphs illustrating the sizes of nanoparticles according to the dynamic light scattering (DLS) analysis.
Figure 3:
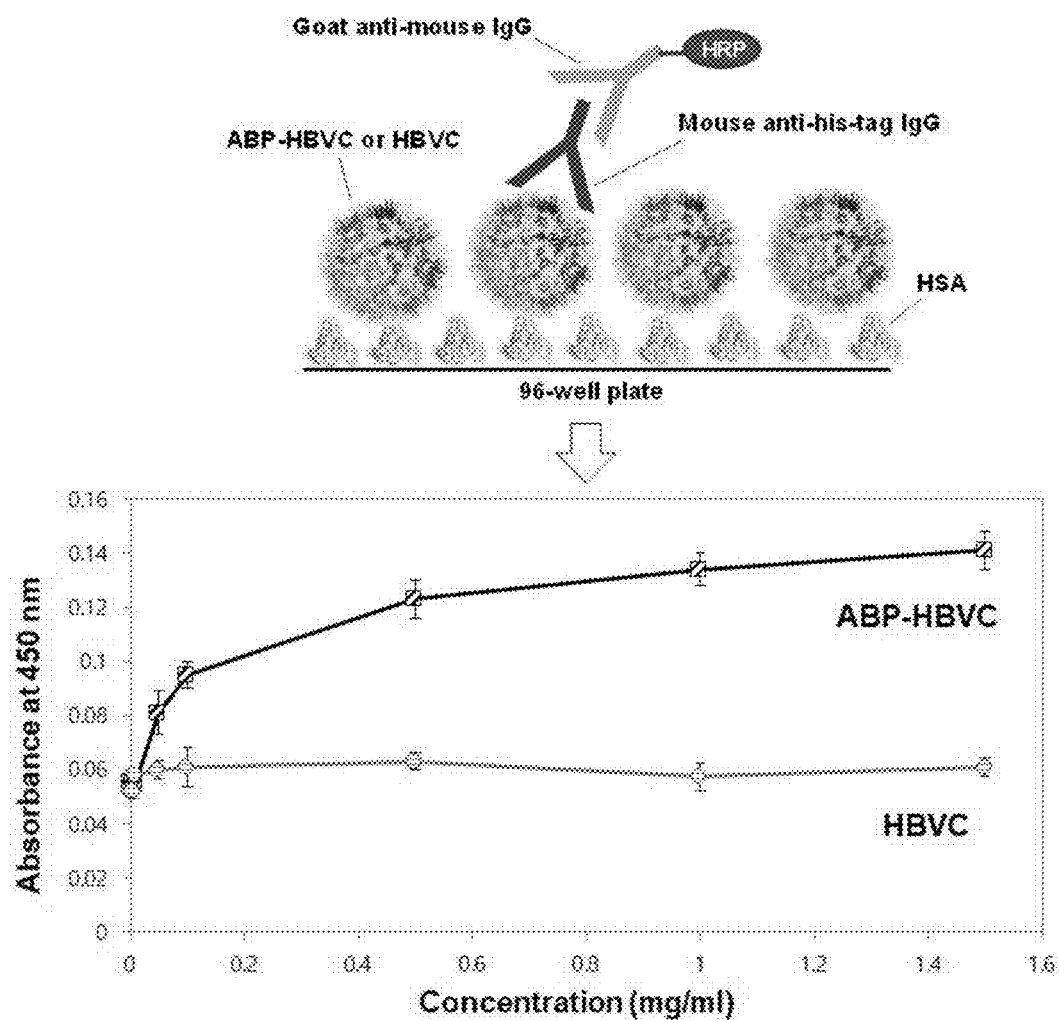
FIG. 3 illustrates ELISA results confirming whether hepatitis B virus capsid protein nanoparticles (HBVC-ABP) including an albumin-binding peptide bind to albumin.

FIG. 2 is a set of transmission electron microscope (TEM) photographs of hepatitis B virus capsid protein nanoparticles (HBVC) and hepatitis B virus capsid protein nanoparticles (HBVC-ABP) including an albumin-binding peptide and a set of graphs illustrating the sizes of nanoparticles according to the dynamic light scattering (DLS) analysis.

As can be seen in the TEM photographs, it was confirmed that spherical nanoparticles were formed, and through the dynamic light scattering (DLS) analysis, it was confirmed that the HBVC and the HBVC-ABP were formed as spherical nanoparticles having a size of 34.3±4.2 nm and 38.4±2.5 nm, respectively.

[Example 5] Proof of Presence or Absence of Binding of Prepared Protein Nanoparticle HBVC-ABP with Albumin Through ELISA First, 2 ug/ml human serum albumin (HSA) was bound onto a 96-well high binding plate. And then, the plates to which HSA was bound were treated with hepatitis B virus capsid protein nanoparticles (HBVC) at various concentrations and hepatitis B virus capsid protein nanoparticles (HBVC-ABP) (0.001, 0.005, 0.01, 0.05, 0.1, 0.5, 1.0, and 1.5 mg/ml) including an albumin-binding peptide, and allowed to react for 1 hour. Subsequently, anti-His tag primary antibodies were bound for 1 hour, and then secondary antibodies to which HRP had been bound were bound for 1 hour, and then a TMB solution was added to each well. The change in color after the treatment with the TMB solution was observed, and it was confirmed whether the ABP bound to actual albumin by measuring absorbance at 450 nm.

FIG. 3 illustrates ELISA results confirming whether hepatitis B virus capsid protein nanoparticles (HBVC-ABP) including an albumin-binding peptide bind to albumin. It can be seen that the hepatitis B virus capsid protein nanoparticles (HBVC) do not bind to albumin, and thus there is no change in absorbance, whereas the absorbance is increased by the binding of the hepatitis B virus capsid protein nanoparticles (HBVC-ABP) including the albumin-binding peptide to albumin as the treatment concentration thereof is increased.

[Example 6] Verification of Presence or Absence of Binding of Prepared Protein Nanoparticle HBVC-ABP with Actual Albumin in Serum After B hepatitis virus capsid protein nanoparticles (HBVC) and hepatitis B virus capsid protein nanoparticles (HBVC-ABP) including an albumin-binding peptide were introduced into human sera, the interaction of proteins in sera was measured through size comparison using the DLS.

Figure 4A:
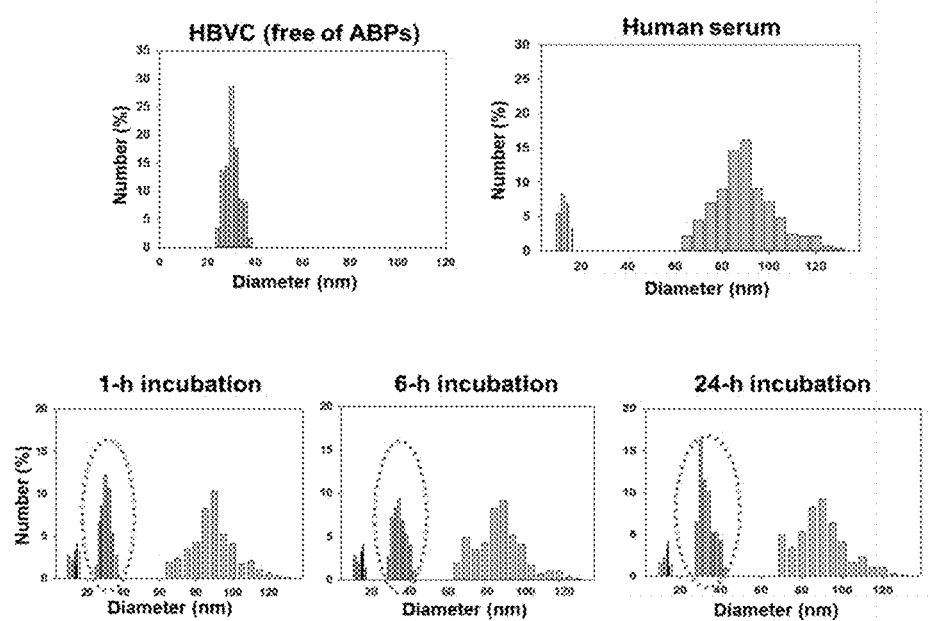
FIG. 4A illustrates results of measuring the interaction of proteins in sera through size comparison using DLS after B hepatitis virus capsid protein nanoparticles (HBVC) (FIG. 4A) are introduced into actual human sera.
Figure 4B:
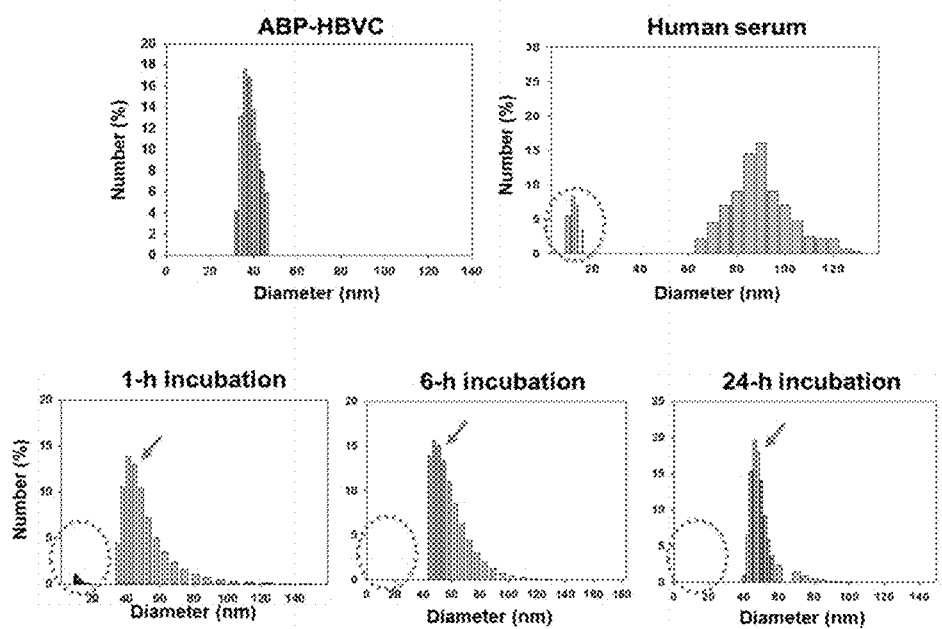
FIG. 4B illustrates results of measuring the interaction of proteins in sera through size comparison using DLS after hepatitis B virus capsid protein nanoparticles (HBVC-ABP) including an albumin-binding peptide are introduced into actual human sera.

FIG. 4 illustrates results of measuring the interaction of proteins in sera through size comparison using the DLS after B hepatitis virus capsid protein nanoparticles (HBVC) (FIG. 4A) and hepatitis B virus capsid protein nanoparticles (HBVC-ABP) including an albumin-binding peptide (FIG. 4B) are introduced into actual human sera.

It can be confirmed that in the serum mixed with the HBVC, the HBVC peak is maintained even after 24 hours, whereas in the serum mixed with the HBVC-ABP, the HBVC-ABP particle peak disappears within 1 hour after the reaction. It can be seen that the HBVC-ABP particles bind to albumin in serum to increase particle size, and thus the peak thereof appears while being mixed with the protein peak present at the rear part. (FIGS. 4 (A) and (B))

[Example 7] Verification of Immunogenicity of Prepared Protein HBVC-ABP

After it was proved through the Examples that HBVC-ABP actually bound to albumin, it was proved through an in vivo experiment whether the ABP expressed on the surface of the HBVC, which has various advantages when injected in vivo, but is limited in use due to high immunogenicity, could reduce the immunogenicity of the HBVC by binding to albumin in vivo.

Example 7-1

Interleukin-1 beta is a cytokine induced when a foreign material is injected in vivo to activate an in vivo macrophage by an immune response. Accordingly, it was intended to observe an increase or decrease in immunogenicity due to the injection of the foreign material by measuring the concentration of interleukin-1 beta.

Figure 5A:
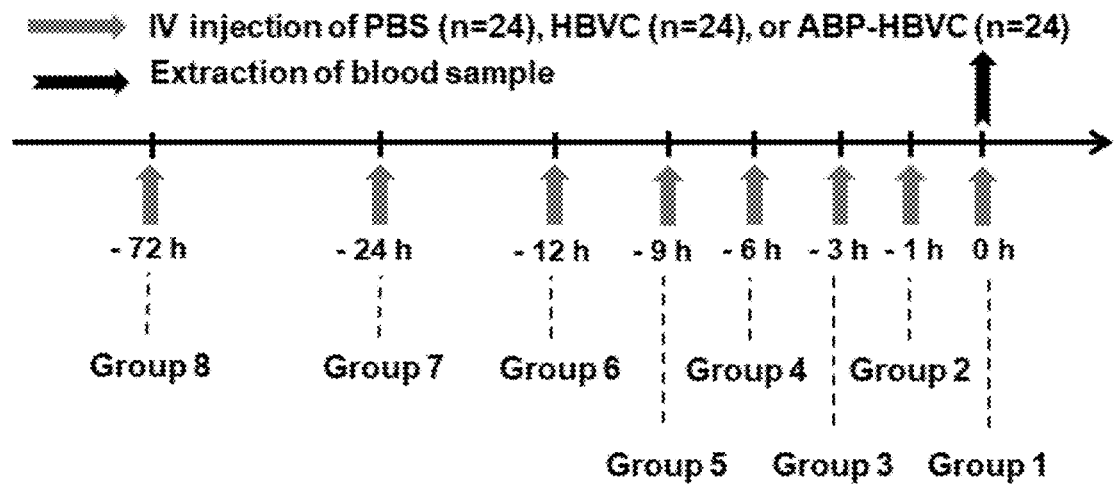
FIG. 5A is a result illustrating the establishment of experimental groups for an in vivo experiment of B hepatitis virus capsid protein nanoparticles (HBVC) and hepatitis B virus capsid protein nanoparticles (HBVC-ABP) including an albumin-binding peptide.
Figure 5B:
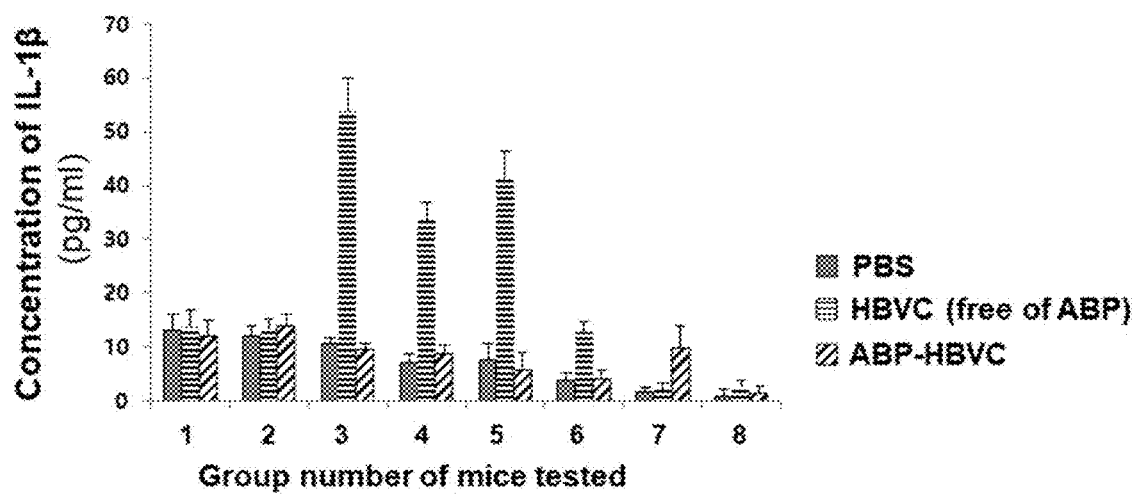
FIG. 5B is the blood concentration (FIG. SB) of interleukin-1 beta of each experimental group in FIG. 5A.

FIG. 5 is a result illustrating the establishment (FIG. 5A) of experimental groups for an in vivo experiment of B hepatitis virus capsid protein nanoparticles (HBVC) and hepatitis B virus capsid protein nanoparticles (HBVC-ABP) including an albumin-binding peptide and the blood concentration (FIG. 5B) of interleukin-1 beta of each experimental group.

A control PBS, HBVC, and an experimental group HBVC-ABP material were injected intravenously into three animals per group at a concentration unit of 0.5 mg/ml for units of 3 days, 1 day, 12 hours, 9 hours, 6 hours, 3 hours, and 1 hour, and then finally, blood of all the experimental groups was collected. Thereafter, the change in concentration of an in vivo cytokine induced by HBVC and HBVC-ABP was measured as time passed after the material was injected using an ELISA kit (Mouse IL-Iβ ELISA Ready-SET-Go!, Cat. No. 88-7013-22, eBioscience) capable of detecting interleukin-1 beta.

Example 7-2

Antibody titer measurement is the most commonly used method for measuring the immunogenicity of the current material. When a foreign material is injected in vivo, an antibody against the corresponding foreign material is induced, so that the immunogenicity of the foreign material may be inferred by the amount of induced antibody.

Figure 6A:
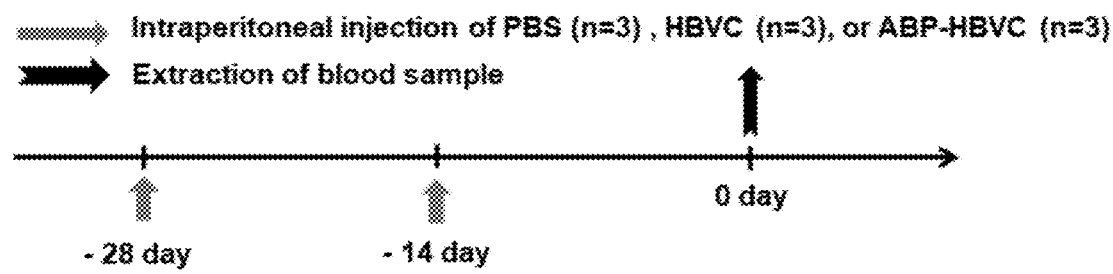
FIG. 6A is a result illustrating the establishment of experimental groups to investigate in vivo antibody induction according to the injection of protein nanoparticles.
Figure 6B:
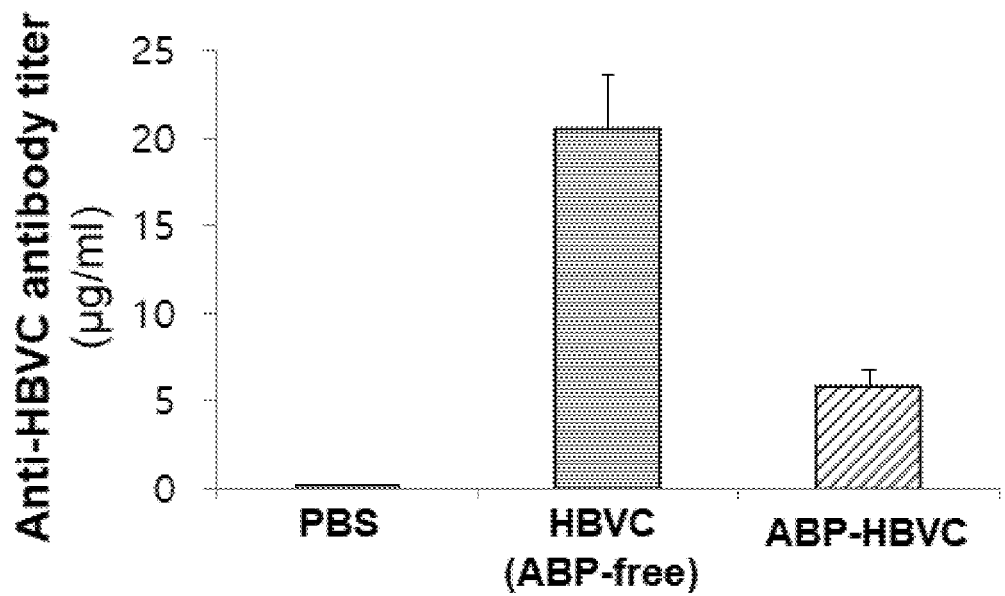
FIG. 6B is the in vivo antibody concentration of each experimental group in FIG. 6A.

FIG. 6 is a result illustrating the establishment (FIG. 6A) of experimental groups to investigate the in vivo antibody induction according to the injection of protein nanoparticles and the in vivo antibody concentration (FIG. 6B) of each experimental group.

A control PBS, HBVC, and an experimental group HBVC-ABP material were injected intraperitoneally into three animals per group at a concentration unit of 0.5 mg/ml twice at an interval of 2 weeks, and then finally, blood of all the experimental groups was collected. Thereafter, in order to detect the antibodies induced by HBVC and HBVC-ABP, 2 ug/ml HBVC was bound to a 96-well plate (Nunc Maxisorp™ ELISAplate), and then anti-HBVC and anti-HBVC-ABP antibodies present in blood were induced to bind by reacting the extracted blood therewith. As a result of induction, it was confirmed that HBVC-ABP particles could actually induce the effect of reducing immunogenicity by verifying that antibodies induced by HBVC particles were present in a larger amount in blood than antibodies induced by HBVC-ABP.

[Example 8] Verification of Cancer Targeting Capability Through NIR Image Analysis of Prepared Protein In order to verify the cancer targeting capability of the albumin-binding peptide, the cancer target capabilities of HBVC protein nanoparticles (also represented by HBVC (aff−, ABP−)) and HBVC-ABP protein nanoparticles prepared in the Examples, and protein nanoparticles (hereinafter referred to as HBVC (aff+)) prepared by replacing the spike site with a tandem sequence of an affibody peptide having strong and specific affinity for human epidermal growth factor receptor I (EGFR) instead of the albumin-binding peptide were compared with one another. EGFR is overexpressed on the surface of a wide range of tumor cells including U87MG. On the surfaces of HBVC, HBVC-ABP protein nanoparticles, and HBVC (affi+) protein nanoparticles, a fluorescent material Cy 5.5 was attached. After the degrees of fluorescence of the prepared materials were uniformly adjusted, the material was administered intravenously to U87MG(glioblastoma)-bearing 5-week-old nude mice, and then the mice were monitored at predetermined time points for 24 hours using an IVIS spectrum imaging system (Caliper Life Sciences, Hopkinton, MA).

Figure 7A:
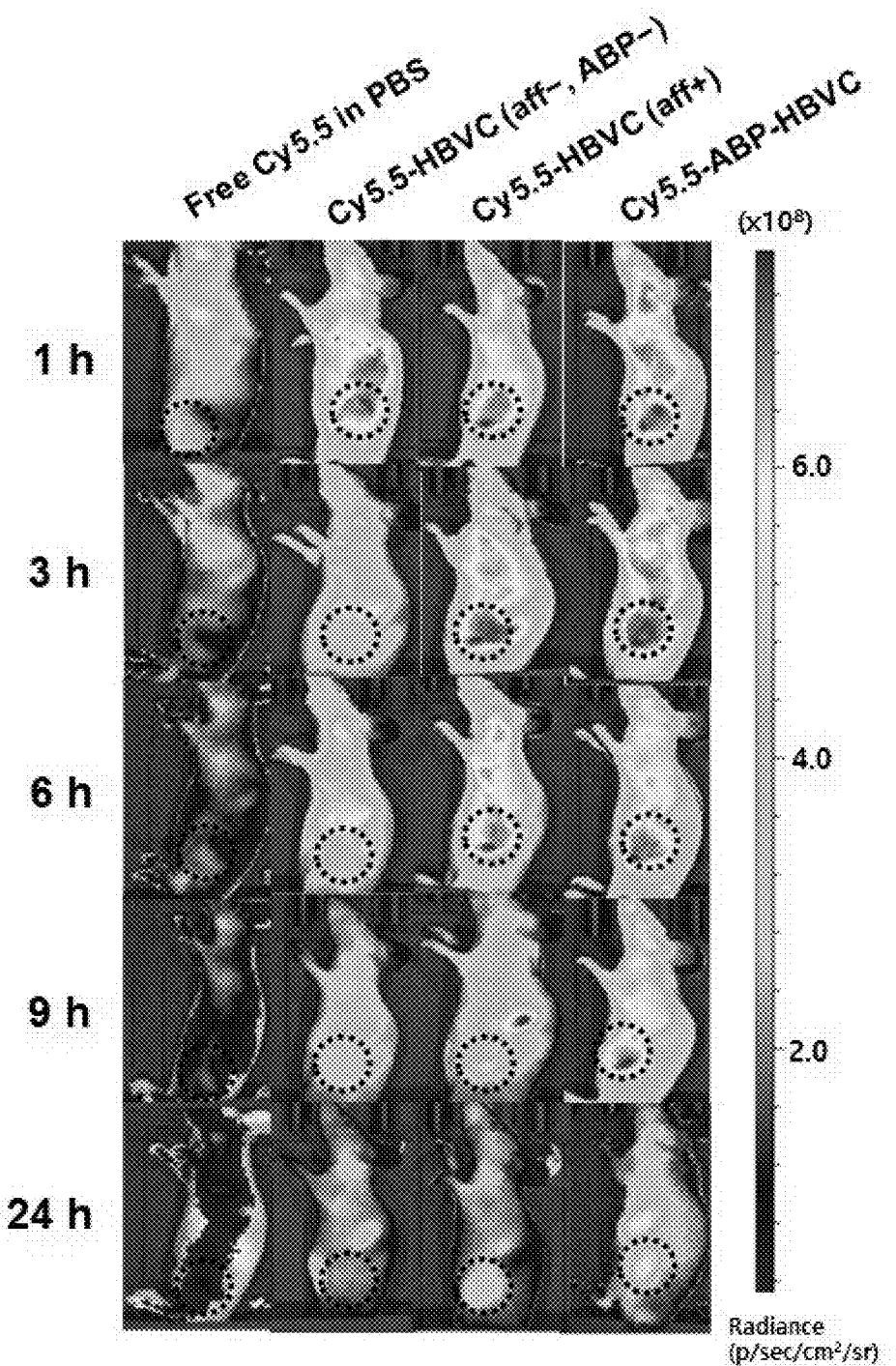
FIG. 7A illustrates NIR fluorescence images of mice intravenously injected with recombinant HBVC particles labeled with Cy 5.5.
Figure 7B:
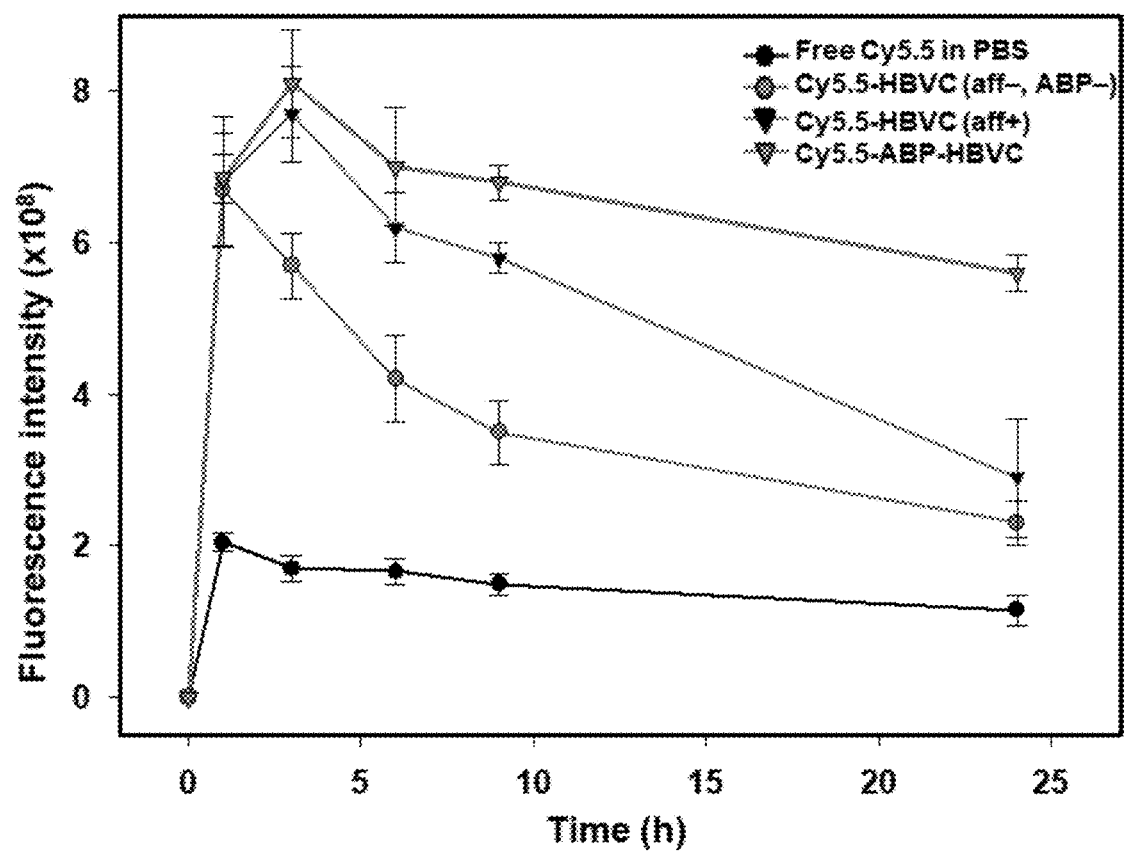
FIG. 7B illustrates the NIR fluorescence intensity over time from tumors in the mice of FIG. 7A.
Figure 7C:
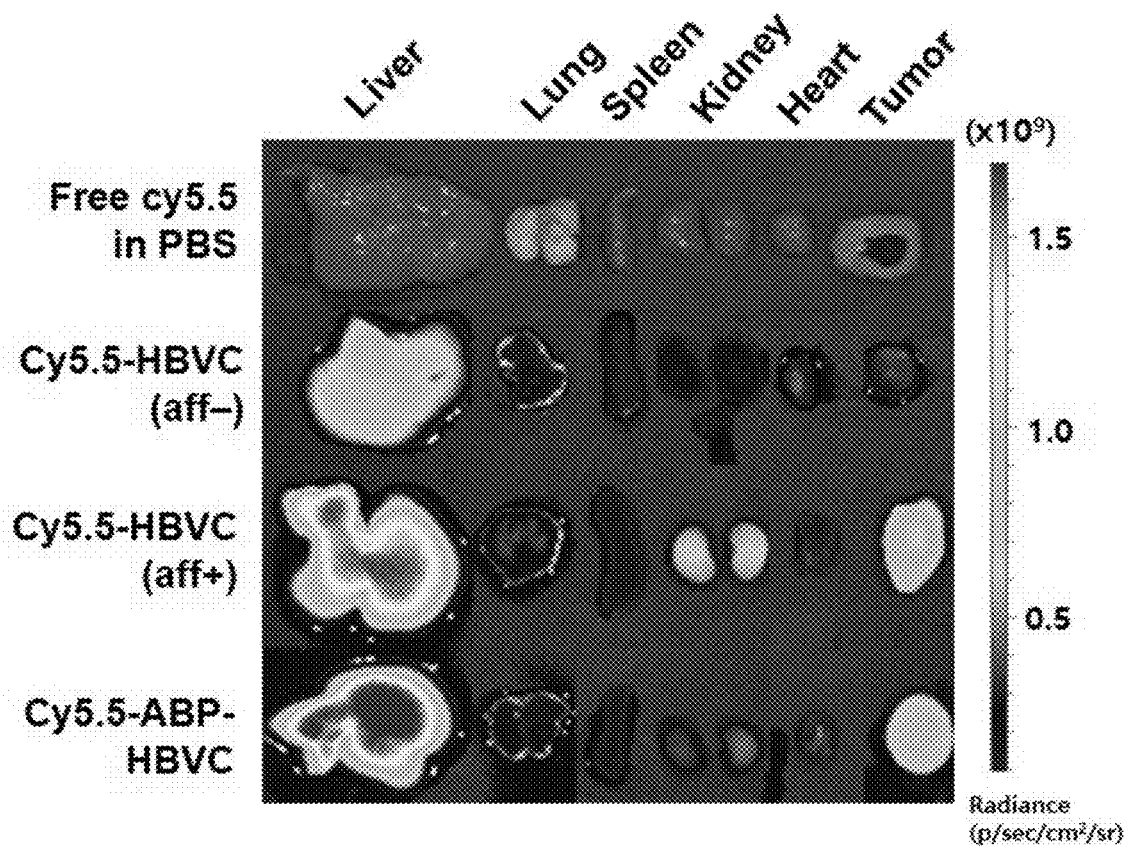
FIG. 7C illustrates an ex vivo near-infrared fluorescence image of 5 major organs and tumors extracted from mice after the intravenous injection.

FIG. 7 illustrates the tumor targeting and in vivo distribution of HBVC-ABP in mice. FIG. 7A illustrates NIR fluorescence images of mice intravenously injected with recombinant HBVC particles (HBVC (aff−, ABP−), HBVC (aff+), and ABP-HBVC) labeled with Cy 5.5. FIG. 7B illustrates the NIR fluorescence intensity over time from tumors in the mice of FIG. 7A. FIG. 7C illustrates an ex vivo near-infrared fluorescence image of 5 major organs and tumors extracted from mice at the time point of 48 hours after the intravenous injection.

As can be seen in FIGS. 7A and 7B, remarkably large amounts of Cy5.5-ABP-HBVC and HBVC (aff+) were delivered to tumors as compared to Cy5.5-HBVC (aff−, ABP−) (no affibody and albumin-binding peptide), and in particular, ABP-HBVC was retained longer in tumors. This suggests that the role of serum albumin as a major energy and nutrient source for tumor growth will prolong the retention of ABP-HBVC in tumors and further enhance the tumor targeting performance of ABP-HBVC. In addition, since the albumin-binding peptide binds to albumin, the albumin-binding peptide has a longer half-life in vivo than other peptides.

The ex vivo near-infrared fluorescence image of 5 major organs and tumors of FIG. 7C shows considerable accumulation of ABP-HBVC and HBVC (aff+) in the liver. EGFR is also expressed at high levels on the surface of hepatocytes, and the liver is a major albumin-producing organ. It can be seen that the amount of ABP-HBVC accumulated in tumors is much larger than the amount of the albumin-binding peptide-free HBVC (aff−, ABP−). Furthermore, a remarkable amount of HBVC (aff+) was detected in the kidneys, indicating that HBVC (aff+) is removed from the body by kidney excretion more rapidly than ABV-HBVC.

For the recombinant self-assembling protein nanoparticles according to the present invention, an albumin-binding peptide can reduce the immunogenicity of the recombinant self-assembling protein nanoparticles because the albumin-binding peptide is presented at the surface, and thus binds to an albumin protein present in vivo, and the albumin-binding peptide can also provide the cancer delivery function of the recombinant self-assembling protein nanoparticles because the albumin-binding peptide binds to albumin around cancer. Simultaneously, the binding of the albumin-binding peptide to albumin can significantly increase the in vivo residence time of the recombinant self-assembling protein nanoparticles, thus increasing the potential for use in various medical applications.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

REFERENCE TO AN ELECTRONIC SEQUENCE LISTING

A sequence listing electronically submitted with the present application on Sep. 19, 2023 as an ASCII text file named 20230919_Q35720LC22T_TU_SEQ.TXT, created on Sep. 19, 2023 and having a size of 3,666 bytes, is incorporated herein by reference in its entirety.

What is claimed is:

1. A recombinant self-assembling protein nanoparticle, comprising:
a self-assembling protein fused with an albumin-binding peptide at a site of the self-assembling protein to locate the albumin-binding peptide at a surface of the self-assembling protein,
wherein the albumin-binding peptide is located at a spike site, the N-terminus or the C-terminus of the self-assembling protein, and
wherein an immunogenic site of the self-assembling protein is shielded by albumin present in vivo,
wherein the albumin-binding peptide has SEQ ID NO: 2.

2. The recombinant self-assembling protein nanoparticle of claim 1, wherein the recombinant self-assembling protein further comprises a linker peptide.

3. The recombinant self-assembling protein nanoparticle of claim 1, wherein the recombinant self-assembling protein further comprises a gold ion adsorbable peptide and a superparamagnetism-inducing peptide.

4. The recombinant self-assembling protein nanoparticle of claim 1, wherein the recombinant self-assembling protein nanoparticle further comprises a target-oriented peptide.

5. The recombinant self-assembling protein nanoparticle of claim 1, wherein the self-assembling protein is a hepatitis B virus core protein, a tobacco mosaic virus protein, a *Thermoplasma acidophilum*-derived proteasome (tPTS), or an *Escherichia coli*-derived DNA binding protein (eDPS).

6. The recombinant self-assembling protein nanoparticle of claim 1, wherein the recombinant self-assembling protein nanoparticle is a hepatitis B virus core protein.

7. The recombinant self-assembling protein nanoparticle of claim 1, wherein the recombinant self-assembling protein is a hepatitis B virus core protein, and the albumin-binding peptide is located at a spike site of the hepatitis B virus core protein.

8. The recombinant self-assembling protein nanoparticle of claim 1, wherein the recombinant self-assembling protein is a hepatitis B virus core protein, and
the albumin-binding peptide is fused to some monomers of the hepatitis B virus core protein.

9. A non-immunogenic pharmaceutical composition comprising: the recombinant self-assembling protein nanoparticle according to claim 1; and
a pharmaceutically acceptable carrier.

10. A contrast agent composition comprising: the recombinant self-assembling protein nanoparticle according to claim 1; a labeling material for imaging; and a pharmaceutically acceptable carrier.

11. A recombinant self-assembling protein nanoparticle, comprising:
a hepatitis B virus core protein (HBVC); and
the albumin-binding peptide of SEQ ID NO: 2 presented at the surface of the HBVC, wherein the albumin-binding peptide is introduced between the 1-77$^{th}$ amino acid sequence part and the 81-148$^{th}$ amino acid sequence part of the hepatitis B virus core protein corresponding to SEQ ID NO: 9.

12. The recombinant self-assembling protein nanoparticle of claim 11, further comprising a linker peptide of G4SG4T introduced between the 1-77$^{th}$ amino acid sequence part of the hepatitis B virus core protein and the albumin-binding peptide and also added to the 148$^{th}$ amino acid sequence of the hepatitis B virus core protein.

* * * * *